(12) United States Patent
Langoju et al.

(10) Patent No.: US 8,054,094 B1
(45) Date of Patent: Nov. 8, 2011

(54) IMAGE RECONSTRUCTION BASED CONSTRAINED MAXIMIZATION

(75) Inventors: Rajesh Veera Venkata Lakshmi Langoju, Bangalore (IN); Manoj Kumar Koyithitta Meethal, Bangalore (IN); Debasish Mishra, Bangalore (IN); Sekethraman Mahalingam, Bangalore (IN)

(73) Assignee: General Electric Company, Niskayuna, NY (US)

( * ) Notice: Subject to any disclaimer, the term of this patent is extended or adjusted under 35 U.S.C. 154(b) by 22 days.

(21) Appl. No.: 12/797,653

(22) Filed: Jun. 10, 2010

(51) Int. Cl.
*G01R 27/08* (2006.01)
(52) U.S. Cl. .................. 324/705; 324/713; 324/722
(58) Field of Classification Search .......... None
See application file for complete search history.

(56) References Cited

U.S. PATENT DOCUMENTS

| 6,940,286 | B2 | 9/2005 | Wang et al. | |
|---|---|---|---|---|
| 7,496,450 | B2 | 2/2009 | Ortiz | |
| 7,498,817 | B2 * | 3/2009 | Redko et al. | 324/464 |
| 2005/0054911 | A1 * | 3/2005 | Nachman et al. | 600/411 |
| 2010/0290675 | A1 * | 11/2010 | Wexler et al. | 382/109 |

FOREIGN PATENT DOCUMENTS

| WO | WO 2009030870 A1 | 3/2009 |
|---|---|---|
| WO | WO 2009006896 | 6/2009 |

* cited by examiner

*Primary Examiner* — Minh N Tang
(74) *Attorney, Agent, or Firm* — Joseph J. Christian (57) ABSTRACT

A method of providing an image of an interior of a structure containing regions having different conductivities or admittivities. In one embodiment a series of electrical signal sets is applied to a series of electrodes, each signal set generating a rotating electric field. A measured set of electrical signals obtained from the electrodes are used to calculate a conductivity or admittivity distribution representative of the interior of the structure in a region about which the electrodes are positioned. The process of calculating the distribution includes defining a cost function, e.g., the energy function based on the distribution, and a forward model expressing the measured set of electrical signals as a function of the change in voltage values with respect to conductivity or admittivity and requiring that the partial derivative of the difference between the energy function and a function based on the forward model equal zero.

14 Claims, 3 Drawing Sheets

IMAGE RECONSTRUCTION BASED CONSTRAINED MAXIMIZATION

BACKGROUND

This invention relates generally to image reconstruction and, specifically, to methods for generating image data based on Electrical Impedance Tomography.

The principles of electrical impedance tomography (EIT) are based on knowledge that media under examination have variations in electrical properties, e.g., conductivities and permittivities, which are highly correlated with material characteristics such as density or chemical composition. For example, in the human body there are significant variations in electrical conductivity among body tissues.

In industrial activities and other non-clinical applications, it is desirable to perform non-invasive monitoring and, sometimes, imaging to determine the composition of a body volume, or to characterize the size and shape of a feature, or other condition within an object of interest. Generally, EIT is useful for imaging features within a volume that are characterized by distinguishable electrical properties. Oftentimes features within volumes having different densities can be resolved on this basis. For example, in multiphase fluid mixtures it is known that conductivities will vary based on phase (e.g., liquid or gas) or chemical composition. In principal, electrical measurements performed with relatively simple instrumentation can provide data indicative of where in the volume a particular material is located, and the relative proportions of different constituents. Examples of mixtures for which phase concentrations can be determined are solid-liquid compositions such as slurries, gas-liquid compositions such as present in oil pipe lines, and, generally, liquid-liquid and solid-gas-liquid mixtures. The mixtures may be stationary or flowing. In the case of fluids flowing through a pipe, conductivity determinations among materials of different phases, or between materials having different chemical properties (e.g., water and oil), can lead to determinations of relative volumes present. In the past, volume fractions of liquid and gas phases in a pipe have been inferred based on electrical impedance measurements. With respect to EIT imaging it is conventional to acquire data by placing a series of electrodes along the periphery of a body under study, e.g., in a circle along an interior surface of a pipe. See U.S. Pat. Nos. 4,486,835; 4,539,640; 4,920,490; and 5,381,333, all of which are incorporated herein by reference. In the measurement systems described by the foregoing literature the measured voltage or current signals are used to reconstruct spatial features within the volume under study so that an image representative of the features can be generated. In this regard, there is what is often referred to as an inverse problem wherein there may not be a unique solution, i.e., image, corresponding to the acquired data. To overcome this it is necessary to impart a relatively large number of sets of excitation patterns to the electrodes. With this data, algorithms are applied to find a conductivity distribution.

When the electrodes are positioned along a plane cutting through the body under study, the algorithms may provide a conductivity distribution along the same plane. Generally, a wide variety of mathematical methods and numerical techniques have been applied to determine a conductivity distribution which resembles that of the body under examination. Extensive computations have been required in order to generate useful image resolutions. It is desired to find techniques by which satisfactory image generation can be had with fewer computations performed in shorter periods of time in order to bring EIT-based image reconstruction to a larger array of commercial applications.

BRIEF DESCRIPTION OF THE INVENTION

According to an embodiment of the invention, a method provides an image of an interior of a structure containing multiple regions having different conductivities. In one embodiment a series of electrical signal sets is sequentially applied to a series of electrodes, each signal set generating a rotating electric field within the structure. A measured set of electrical signals is obtained from the electrodes which sets are used to calculate a conductivity distribution representative of the interior of the structure in a region of the structure about which the electrodes are positioned. The process of calculating the conductivity distribution includes defining a cost function (for example, an energy function) based on the conductivity distribution and a forward model expressing the measured set of electrical signals as a function of the change in voltage values with respect to conductivity and requiring that the partial derivative of the difference between the energy function and a function based on the forward model equal zero. See Equations 6-12, below.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

The invention is now described in an application where imaging can be used to determine proportions of components in a multiphase flow where more than one material is flowing together inside a pipe or a conduit. Embodiments of the present invention function to provide a system and a method for measuring the characteristics of multi-material systems, such as those used in the oil industry, to estimate fractions and flow rates of oil, water, and hydrocarbon gases flowing through pipes. Although the invention is described with reference to a use in oil/gas/water measurements, it is by no means limited to such applications. Rather, the invention is applicable to a wide variety of industrial, healthcare and chemical processes such as, for example, medical imaging, cancer diagnosis and water treatment processes.

Material flowing through the pipe may be in multiple ones of the physical states of solid, liquid and gas. Accurate characterization of multiphase flow processes enables improved design and increased operational efficiencies of systems and processing equipment used in the petroleum, pharmaceutical, food, and chemical industries. Relevant flow characteristics used to predict performance of multiphase processes may include, for example, spatial distribution of the phases (spatial volumetric phase fractions), flow regime, interfacial area, and absolute and relative velocities between the phases or materials. With a determination of the non-uniform spatial distribution of materials in a multi-phase flow, it becomes possible to manage and control the process for a more desirable outcome. For example, in a pipeline carrying petroleum products the proportion of gas relative to liquid constituent may be minimized. In coal slurry transport, the volumetric proportion of water to coal can be optimized to assure maximum achievable energy content per unit volume. As another example applicable to optimizing manufacturing processes, it is important to monitor and reduce non-uniform distributions of materials undergoing chemical reaction or conversion. Such processes may have reduced interfacial area between materials due to, for example, recirculating flows that create spatially non-uniform reaction zones or concentrations.

Thus real-time knowledge of volumetric phase fractions and associated components enable timely and effective control of multi-phase flows. However, computational requirements to generate such characterizations can add undue complexity and may delay the response time needed to implement timely control of the process being monitored. For this reason many of the prior systems have relied upon approximations to determine the material proportions and to characterize the separation of materials in a multi-phase system.

In the past, image reconstruction using EIT has been based on sequentially providing input signals to pairs of electrodes and sensing signals at one or more other electrodes. For example, currents may flow between a pairs of electrodes, one pair at a time, with voltages being measured on the remaining electrodes. Alternately, voltages may be applied across the pairs of electrodes, one pair at a time, with current measured at one or more of the other electrodes. Example embodiments are configured to produce relatively large amounts of electrical data quickly by simultaneously applying currents or voltages to all of the electrodes. The applied currents or voltages may have predefined phase or frequency shifts or may be electrically in phase with each other and may have amplitude variations. In the past, longer processing time has been needed to perform the reconstruction based on the larger number of current or voltage patterns applied to electrodes. On the other hand, with generation of the increased amount of electrical data, it is possible to realize a higher signal-to-noise ratio and a higher resolution. This is especially relevant when the body under examination comprises components with small variations in relative permittivities or conductivities are involved as a relatively larger number of measurements are needed to provide necessary resolution.

Figure 1:
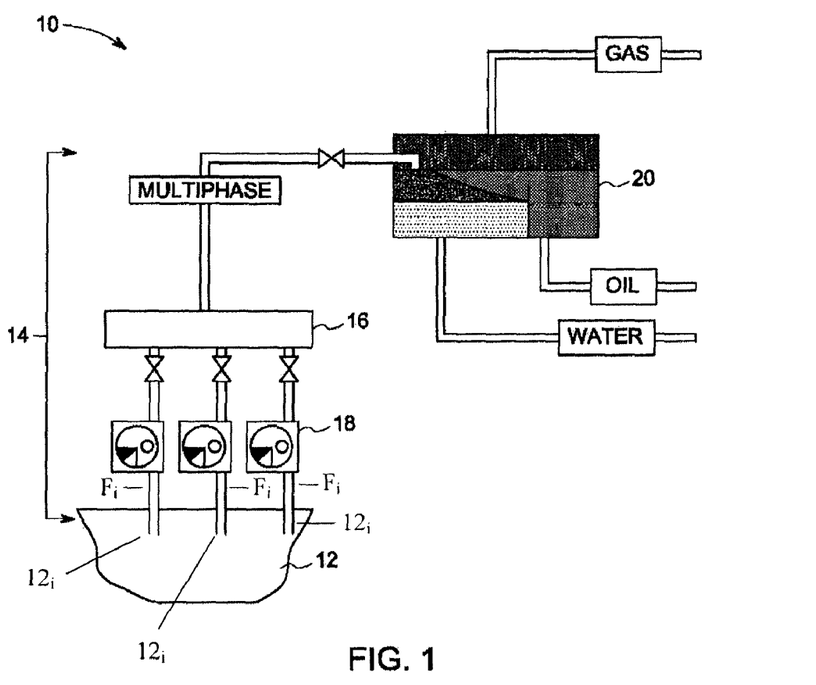
FIG. 1 is a block diagram of a oil production facility according to an example embodiment.

With reference to the simplified schematic illustrated in FIG. 1, an example embodiment of the invention is described for a typical oil production facility 10 having multiple oil wells 12, connected to a piping system 14. The piping system 14 includes a production manifold 16 coupled to receive flow $F_i$ from each well 12, and output a total flow F. The flow $F_i$ from each well passes through a multi-phase flow meter (MPFM) 18 before entering the manifold 16 and may be controlled by a valve system to regulate the overall proportion of, for example, liquid and gaseous phases.

Each multi-phase flow meter is part of a system which enables measurement of unprocessed well streams very close to the well and can thus provide continuous monitoring of well performance. Information processed by each multi-phase flow meter system may be used for better reservoir management and flow control. Fluids pumped from the oil wells $12_i$ are sent to a production separator 20 through the production manifold 16. A test separator (not shown) may be incorporated with the multiphase flow meter systems. One advantage of a multiphase flow meter system over a test separator is the reduced time needed to characterize the composition of the flow.

The production separator 20 separates oil, gas, and water pumped from the wells. The production separator 20 may further include one or more measurement devices. The measurement devices may include, for example, a water meter to measure an amount or rate of water extracted from a well and an emulsion meter to measure an amount of oil extracted from the well. Further measurement devices may be included to monitor well performance, including a wellhead pressure sensor and a thermometer.

Figure 2:
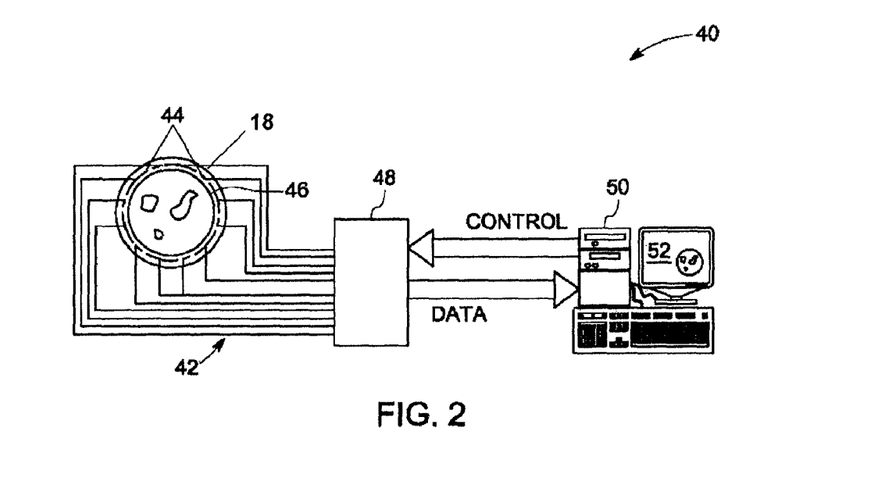
FIG. 2 is a schematic of an electrical impedance tomography (EIT) based multiphase flow meter to be used in accordance with an embodiment of the present invention.

Next referring to the simplified schematic diagram of FIG. 2, there is shown an image reconstruction system 40 including a MPFM 18 based on electrical impedance tomography (EIT) and according to an example embodiment of the invention based on conductivity reconstruction. However, it is to be understood that, in principle, EIT image reconstruction may be based on conductivity and/or permittivity (sometimes referred as admittivity). With the system 40, conductivities and/or permittivities of materials being observed are inferred based on boundary electrical measurements taken from electrodes near the periphery of the volume under study as sets of current or voltage signals are applied to the electrodes. According to example embodiments large amounts of data are acquired by sequentially obtaining measurements from all electrodes for each set of signals. That is, measurements are repeated for numerous different configurations or patterns of applied currents and/or voltages.

The MPFM 18 of the MPFM system 40 of FIG. 2 includes an electrode array 42 comprising an arbitrary number, L, of electrodes 44 and wiring distributed around a conduit 46 which, in this application, is of a generally cylindrical shape. Although not expressly shown, the conduit is positioned in line between one of the oil wells $12_i$ and the manifold 16 so that multiphase components pass through the conduit. For purposes of illustrating the invention, the number, L, of electrodes shown in the figure is twelve, but fewer or many more than 12 electrodes may be placed about the conduit for measurement, depending in part on the size of the pipe and the desired image resolution. In one embodiment, each of the electrodes may be mounted along the inner wall of the conduit with an electrical connection from an external signal source passing into the outer wall to connect with the electrode. A coating may be applied to each electrode to reduce contact resistance between the electrode and media flowing through the conduit 46. The array of electrodes 44 is configured in a plane, P, orthogonal to a central axis of symmetry of the cylindrically-shaped conduit 46.

Electrodes in the array 42 are each connected through the wiring to electronic circuitry 48 which includes, e.g., for each electrode: a current or voltage source, a D-to-A-converter, an A-to-D converter, a differential amplifier and one or more filters. The circuitry 48 further includes analog multiplexers, clock circuitry, and/or a digital I/O unit coupled to a computer 50 in order to provide sets of input signals to the electrodes. Specific arrangements for the circuitry 48 are known in the art and not further described herein because illustration of the invention does not require further illustration of circuit designs.

The computer 50 may comprise high end, high speed processors, including a conventional digital signal processor of the type used for the image reconstruction, and a suitable display 52 for viewing images generated according to the invention. Other processing circuitry such as field-programmable gate arrays (FPGA's) and complex programmable logic devices (CPLD's) may be incorporated in the computer 50 or in other portions of the system 40.

When each set of electrical signals is applied to the electrodes 44 a rotating electric field is produced inside the conduit. The following discussion assumes that voltage signals are applied to the electrodes and that current signals are acquired in response thereto in order to generate needed data for image reconstruction. The voltage sources are used to apply each set of patterns to the electrodes 44, and the corresponding set of current signals in each of the electrodes is measured.

Figure 3:
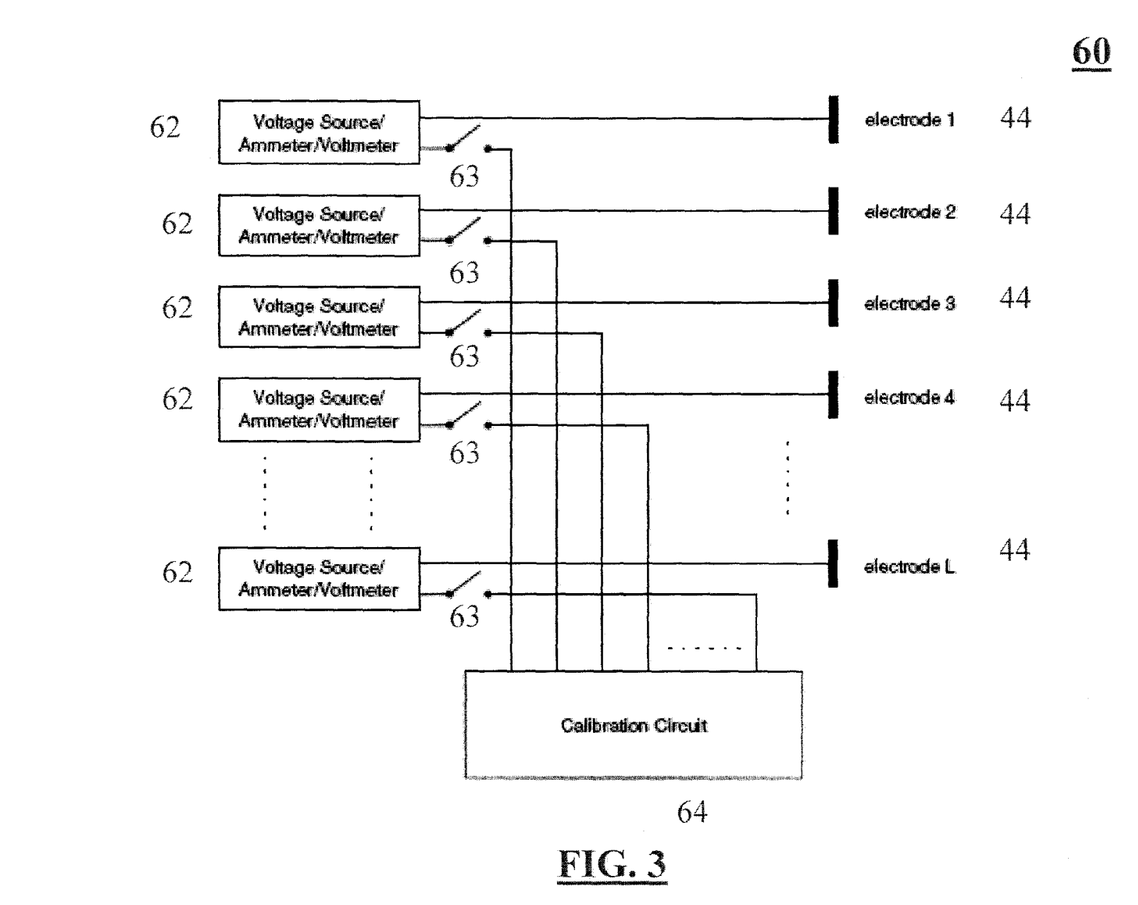
FIG. 3 is a block diagram of an applied-voltage EIT system in accordance with an embodiment of the present invention.

FIG. 3 is a simplified schematic diagram of an applied-voltage EIT system 60 having L electrodes. Each electrode 44 is connected to a circuit 62 that includes a voltage source for generating the applied voltage as well as an ammeter to measure the current, and a voltmeter to directly measure the applied voltage. A switching network 63 enables a single calibration circuit 64 to be connected to any of the voltage source/ammeter/voltmeter circuits to allow the whole system to be calibrated to a single reference source. A digital controller (not shown) interfaces with aforementioned components to operate switching functions including calibration, signal generation and acquisition of measurement data. Measurement data is processed according to the invention by the computer 50 to determine the electrical conductivity distribution in the plane P along which the electrodes are positioned.

The electrical conductivity and permittivity distribution is further processed to determine material characteristics of the multi-phase flow, including distribution of different phases or distribution of different materials in the liquid phase, e.g., oil and water. Analysis of the electrical conductivity distribution may determine flow regimes, phase fractions and velocity of individual components of the multi-material system. The flow regimes may, for example, include bubbly flow, churn flow, slug flow, or annular flow.

In voltage source embodiments, current flow between electrodes is a function of relative voltages applied across all electrodes, the conductivity and permittivity distribution along the plane P about which the electrodes are configured. For example, the material may be only oil or it may be an oil-water liquid mixture as well as a separate gas phase. Depending on the distribution of material constituents, the conductivity and permittivity between electrodes will vary and consequently the level of current between electrodes will also vary. Thus, with application of one or more voltage sets and the corresponding measured current data, a matrix of conductivity values corresponding to the varied conductivity along the plane P can be calculated. Because these conductivity values correspond to the conductivities and permittivities of the materials passing through the plane P, by analyzing the conductivities the material composition or phase flow distribution can be determined.

Each set of voltage patterns is a time varying function which produces a rotating electric field inside the conduit 44, i.e., the electric field changes direction at an angular velocity which is a function of the applied signal frequency, ω, or integer multiples thereof. For a constant frequency ω, the angular velocity with which the field rotates will be constant.

When the rotating electric field is produced by sequentially applying a set of voltage patterns to the L electrodes, the voltage patterns that will be applied across the electrodes can be represented as:

$$V_k^\lambda = \hat{V}\sin\left(\omega t \pm \frac{2\pi\lambda}{L}(k-1)\right) \quad \text{(Eq. 1)}$$

$$V_k^\lambda = \hat{V}\sin\omega t\cos\left(\frac{2\pi\lambda}{L}(k-1)\right) + \hat{V}\cos\omega t\sin\left(\frac{2\pi\lambda}{L}(k-1)\right) \quad \text{(Eq. 2)}$$

$$V_k^\lambda = \hat{V}\sin\omega t\cos\left(\frac{2\pi\lambda}{L}(k-1)\right) - \hat{V}\cos\omega t\sin\left(\frac{2\pi\lambda}{L}(k-1)\right) \quad \text{(Eq. 3)}$$

where $V_k^\lambda$ is the voltage applied to the kth electrode in the $\lambda^{th}$ set of excitation patterns, $\hat{V}$ is a peak voltage of a reference sine wave, t is the time and ω is frequency of the sine wave. Equations (2) and (3) are alternate forms of equation (1) with each corresponding to one of the two + and − alternatives of Equation (1) wherein the plus sign option provides a forward voltage pattern and the negative sign option provides a reverse voltage pattern. A signal set according to Equation (2) generates a forward voltage pattern for clockwise rotation of the electric field inside the conduit 46, whereas a signal set according to Equation (3) generates a reverse voltage pattern for counterclockwise rotation of the electric field inside the conduit. A set of excitation patterns may comprise a set of forward voltage patterns according to Equation (2) or a set of reverse voltage patterns according to Equation (3). In such embodiments λ may range from 1 to L/2, or higher, resulting application of a total of λ sets of forward or reverse voltage patterns being applied to the electrodes 44. In another embodiment, sets of signals applied to the electrodes 44 may comprise both forward and reverse patterns, this resulting in more complete information about the multi-material system. Forward voltage patterns and reverse voltage patterns together provide information about real and imaginary components of electrical elements of the system.

Figure 4:
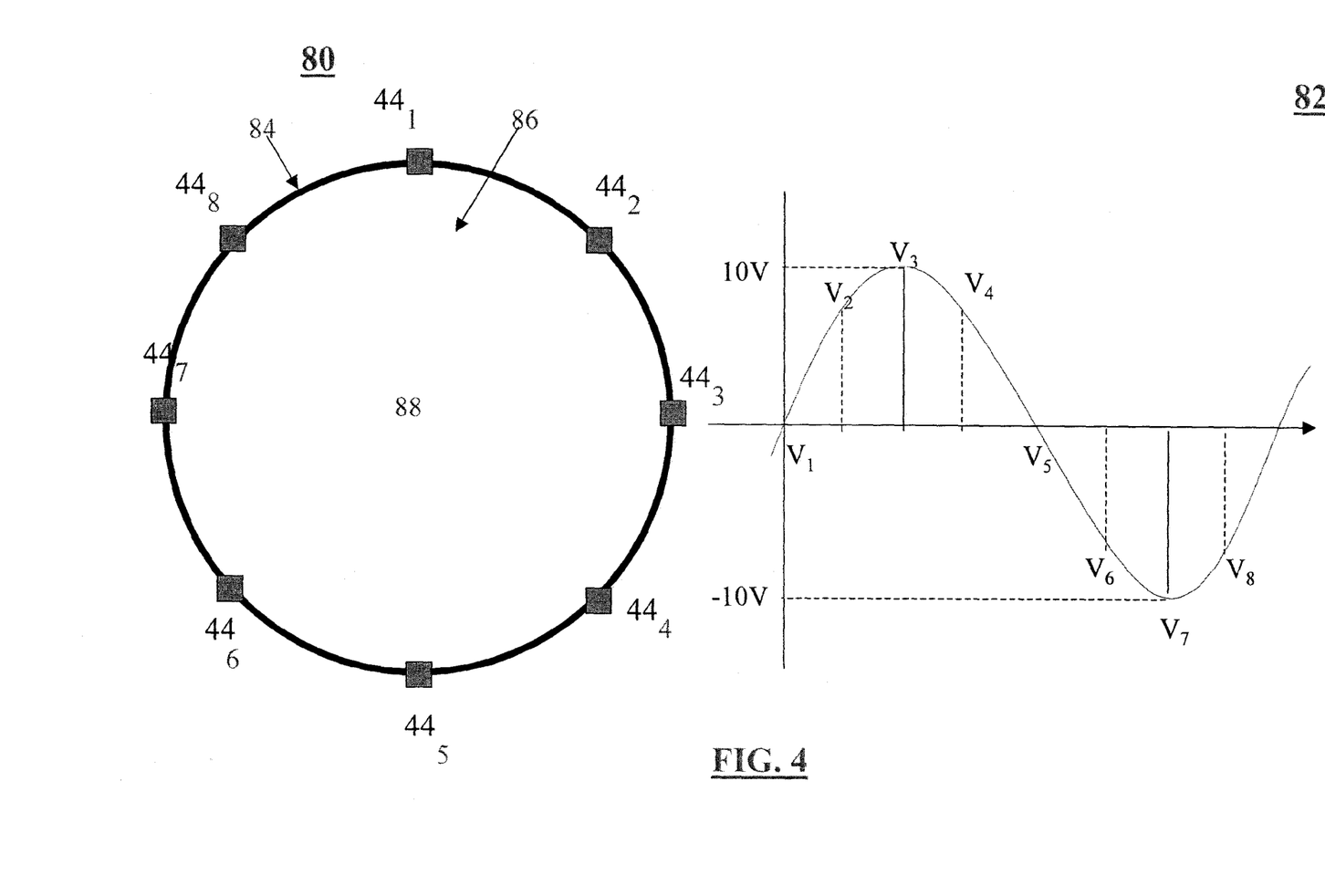
FIG. 4 is a schematic of electrodes across a pipe and a reference sine waveform in accordance with an embodiment of the present invention.

FIG. 4 is a schematic illustration 80 of the electrodes 44, showing for L=8, eight electrodes 44$_i$, for i=1-8. The illustration of L=8 electrodes is exemplary. The electrodes 44$_i$ are uniformly spaced apart in positions along a circle cut by the plane P in the cylindrically shaped conduit 46. FIG. 4 further illustrates a set of waveform values $V_i$, for i=1-8 positioned on a sinusoidal waveform. For a given value of i, each illustrated value $V_i$ corresponds to a signal input to a corresponding electrode 44$_i$. That is, each waveform value $V_i$ is a temporal value which occurs at the same time in a different one of eight time dependent voltage input signals generated in accord with Equation (2) or Equation (3), wherein $\hat{V}$=10V and for the set of applied patterns having λ=1. The differences between voltage amplitudes $V_k^\lambda$ applied to adjacent electrodes in the sequence of eight electrodes 44$_i$ are based on the phase shifts imposed by 2πλ(k−1)/L with k=i and λ=1. Thus the waveform values V1 to V8 are phase-shifted voltage signals simultaneously applied to the electrodes at a given time.

In this example the conduit 46 includes an oil-water emulsion 86 and gas 88 segregated from the emulsion, with the gas flowing in the center region of the conduit 46 and the emulsion 86 surrounding the gas flow. Other sets of voltage patterns may be applied to the electrodes including, for example, second and/or third harmonic voltage patterns as per Equation (2) or Equation (3) with λ equal to 2 and/or 3, respectively.

Per the system 60 of FIG. 3, the circuits 62 dedicated to each electrode, all operating under a common clock signal, each generate a waveform having a distinct phase relative to the phase of the waveform generated for the adjacent electrode. In this regard, the horizontal axis about which the set of waveform values V, are plotted corresponds to an angular position, in the plane P, about the cylindrically-shaped conduit 46, such that at a given time (e.g., time t=0), each of the eight points labeled V1 to V8 on the sine wave corresponds to the magnitude of the applied signal at each electrode. Thus with a phase shift of $2\pi/L$ (for $\lambda=1$) occurring between adjacent ones of the electrodes, the multiple phase-shifted sine waveforms are simultaneously applied to different ones of the equally spaced-apart electrodes and the values V1 to V8 shown on the waveform refer to the instantaneous voltages applied to the eight electrodes at a time, t. Collectively, the eight input signals generate a time varying electric field pattern which rotates in the plane P.

In one embodiment, when only the conductivity distribution is to be determined, the total number of sets of voltage patterns applied to the electrodes to acquire complete information about the phase distribution may be as small as $\lambda=L/2$. The L/2 patterns may be either forward patterns, which produce clockwise rotating electric field, or reverse patterns, which produce anticlockwise rotating electric field.

A data acquisition process according to an embodiment of the invention sequentially applies $\lambda$ sets of voltage patterns to the electrodes 44. In other embodiments, the sets of applied electrical signals may comprise one or more sets of current values and one or more sets of voltage values. For the purpose of better understanding the first electrical signal set is assumed to be a set of voltage values.

For each set of applied voltage patterns a set of electrical signal patterns is measured, e.g., in accord with the system 60 of FIG. 3. An exemplary number of acquired data elements for each set of applied voltage patterns is the product of the number of electrodes and the number of measurements taken per cycle of applied signal for a given value of $\lambda$. With the circuitry 48 of the system 40 including A/D converters, for each voltage excitation pattern a time series of current data is recorded for each of the L electrodes. This time series data is processed to extract amplitudes and phases of currents at all L electrodes. Time series data at each electrode provides one amplitude and one phase value for current at that electrode. Hence for L electrodes there are L measurements. The process in repeated for all $\lambda$ sets of voltage patterns to provide $\lambda L$ elements of measured time series data.

Based on $\lambda L$ elements of measured time series data, a conductivity matrix is determined which is representative of the distribution of material in the conduit 46. Image reconstruction is performed based on the conductivity and or admittivity matrix. For further discussion on exemplary determinations of matrix values indicative of material distribution see U.S. application Ser. No. 12/652,116 hereby incorporated by reference.

According to the invention, determination of the conductivity or admittivity matrix departs from conventional approaches which find the distribution by minimizing the forward model mismatch. Instead, a maximization problem is solved wherein the energy of the conductivity distribution is the objective function subject to the constraint of the forward model mismatch. An example now follows, with $U_{el}$ voltage at each electrode and the forward model defined as $$U_{el}=J(\sigma)*\sigma \quad \text{(Eq. 4)}$$

with J, the Jacobian, being the partial derivative of $U_{el}$ with respect to the conductivity $\sigma$, although $\sigma$ may, in the alternative, represent admittivity.

In matrix form, the forward model is expressed as follows:

$$U_i = \sum_{j=1}^{N} J_{ij}\sigma_j \quad \text{(Eq. 5)}$$

where $U_i$ is a vector comprising a total number of data elements, M, e.g., measured current data, with i=1, 2, 3, . . . M.

The conductivity matrix $\sigma_j$ comprises j elements collectively defining a conductivity distribution to be determined for a region within the conduit 46 and along the plane, P.

The objective function can be selected from a variety of possible energy functions related to the field. Here, we choose as an example, $$P = \sum_{j=1}^{N} \sigma_i^2 \quad \text{(Eq. 6)}$$

That is, the energy of the conductivity distribution is maximized, with the forward model mismatch being the constraint. Specifically, maximization may be achieved using the Lagrange Multiplier Technique wherein $\lambda_i$ denotes the Lagrange Multiplier terms:

$$F(\sigma) = \sum_{j=1}^{N} \sigma_j^2 - \sum_{i=1}^{M} \lambda_i [J_{i,j}\sigma_j - U_i] \quad \text{(Eq. 7)}$$

Accordingly $F(\sigma)$ is made subject to the condition $$\frac{\partial F}{\partial \sigma_j} = 0 \quad \text{(Eq. 8)}$$

It then follows that $$\frac{\partial F}{\partial \sigma_j} = 2\sigma_j - \sum_{i=1}^{M} \lambda_i J_{ij} = 0 \text{ and} \quad \text{(Eq. 9)}$$

$$\sigma_j = \frac{1}{2}\sum_{i=1}^{M} \lambda_i J_{ij} \quad \text{(Eq. 10)}$$

so that the forward model expression becomes $$U_i = \sum_{j=1}^{N} J_{ij}\sigma_j = \frac{1}{2}\sum_{j=1}^{N} J_{ij}\sum_{k=1}^{M} \lambda_k J_{kj} \text{ and} \quad \text{(Eq. 11)}$$

$$g_i = 2U_i = \sum_{j=1}^{N} J_{ij}\sum_{k=1}^{M} \lambda_k J_{kj} \quad \text{(Eq. 12)}$$

(where $U_i$ is the experimentally measured voltage data) which can be solved to find the values of the Lagrange Multipliers, $\lambda_k$, via Gauss-Seidel iterations $$\lambda^{p+1} = \lambda^p + (D^T D + \alpha R^T R)^{-1} D^T (g_{exp} - g_{comp}) \quad \text{(Eq. 13)}$$

for $\lambda^{p+1} - \lambda^p = 0$ for each $\lambda_k$
where:
R is the regularization parameter, each element of D is defined as $$D_{ik} = \left\{\frac{\partial g_i}{\partial \lambda_k}\right\} = \sum_{j=1}^{N} J_{ij} K_{kj} \quad \text{(Eq. 14)}$$

α is a regularization parameter
$g_{exp} = g_i$,
$g_{comp} = 2U_{comp}$, where $U_{comp}$ is the voltage data computed using the Forward model $U_{el}J(\sigma)\sigma$
and the terms $D^T$ and $R^T$ are transposes of D and R, respectively.

A method has been described for displaying an image of an interior of a structure which may be a medical image of organs or other portions of a human body but, more generally, an image of features within a volume characterized by different electrical properties such as multi-phase fluids (e.g., the materials include oil and a hydrocarbon gas) flowing through a conduit, or a volume containing multiple regions having different conductivities which influence transmission of electrical signals through the volume. The determined image information may be used to estimate relative proportions of liquid and gaseous material flowing through the conduit.

A feature of embodiments of the invention is provision of a series of electrical signal sets for input to electrodes positioned along a plane, with each signal set comprising an electrical signal pattern for input to each of the electrodes. With the structure including two or more regions having different conductivities the invention determines an image representative of the interior of the structure in a manner with a more computationally efficient approach to image generation with electrical impedance tomography.

By way of comparison, in using a Newton One Step Error Reconstructor technique, the iterative inverse solver requires intense computational solving for all of the N elements of the conductivity distribution while the aforedescribed process solves for M Lagrange Multipliers $\lambda_k$. That is, with the number of elements, N, in the conductivity matrix being much larger than the number of acquired measurements, M, the conventional reconstruction approach, of iteratively finding a solution based on the difference between the forward model and measured data, requires finding N solutions with iterative techniques.

In disclosed embodiments of the invention the series of applied electrical signal sets each comprise voltage input patterns and the measured electrical signal sets each comprises measured current levels. In other embodiments the series of applied electrical signal sets each comprise current input patterns and the measured electrical signal sets each comprise measured voltage levels. In still other embodiments some in the series of applied electrical signal sets comprise voltage input patterns while others in the series of applied electrical signal sets comprise current input patterns, and some of the measured electrical signal sets comprise measured current levels while others of the measured electrical signal sets comprise measured voltage levels.

The inventive method has been described for a conduit defining a volume that is generally cylindrical in shape, but the invention is applicable to structures of varied shapes including body cavities and body masses of varied sizes and shapes. Also, a single array of electrodes has been described while it is contemplated that signal sets may be simultaneously or sequentially applied to multiple spaced-apart electrode arrays (e.g., in along planes cutting through the structure under examination, and arrangements are also contemplated wherein the electrodes and the structure may be displaced relative to one another in order to generate image information associated with different portions of the volume under investigation.

While only certain features of the invention have been illustrated and described herein, many modifications and changes will occur to those skilled in the art. It is, therefore, to be understood that the appended claims are intended to cover all such modifications and changes as fall within the true spirit of the invention.

The claimed invention is:

1. A method of providing an image of an interior of a structure containing multiple regions having different conductivities or admittivities which influence transmission of electrical signals through the structure, comprising:
   providing a series of electrodes along a plane passing through the structure, with the electrodes positioned along an external surface of the structure;
   providing a series of electrical signal sets for input to the electrodes, each signal set comprising an electrical signal pattern for input to each of the electrodes;
   sequentially applying each of the electrical signal sets to the electrodes, application of each signal set generating a rotating electric field within the structure;
   obtaining, in response to application of each signal set, a measured set of electrical signals from the electrodes;
   calculating, with the measured set of electrical signals, a conductivity or admittivity distribution representative of the interior of the structure in a region of the structure about which the electrodes are positioned; and
   determining image data representative of the interior of the structure including two or more regions having different conductivities or admittivities, wherein the process of calculating the conductivity or admittivity distribution includes defining an energy function based on the conductivity distribution and a forward model expressing the measured set of electrical signals as a function of the change in voltage values with respect to conductivity and requiring that the partial derivative of the difference between the energy function and a function based on the forward model equal zero.

2. The method of claim 1, wherein the series of applied electrical signal sets each comprises voltage input patterns and the measured electrical signal sets each comprise measured current levels.

3. The method of claim 1, wherein the series of applied electrical signal sets comprises voltage input patterns and the measured electrical signal sets comprise measured current levels.

4. The method of claim 1 wherein the structure is a conduit through which materials having different conductivities flow.

5. The method of claim 4 wherein the materials include oil and a hydrocarbon gas.

6. The method of claim 4 wherein image information is used to determine relative proportions of liquid and gaseous material flowing through the conduit.

7. The method of claim 1 wherein the structure is a conduit through which materials having different phases flow.

8. The method of claim 7 wherein the materials include oil and a hydrocarbon gas.

9. The method of claim 7 wherein image information is used to determine relative proportions of liquid and gaseous material flowing through the conduit.

10. The method of claim 1 wherein the applied signal sets comprise λ sets of voltage excitation patterns, each pattern applied to one of L electrodes (L=1–k), and the voltage patterns are generated in accord with $$V_k^\lambda = \hat{V}\sin\left(\omega t \pm \frac{2\pi\lambda}{L}(k-1)\right)$$

where $V_k^\lambda$ is a time varying voltage sine wave applied to the kth electrode in the $\lambda^{th}$ set of excitation patterns, $\hat{V}$ is a peak voltage of a reference sine wave, t is the time and $\omega$ is the frequency of the sine wave.

11. The method of claim 10 wherein the measured set of electrical signals comprises at least $\lambda L$ elements of measured data used to determine the conductivity distribution.

12. The method of claim 1 wherein:
   the process of calculating the conductivity or admittivity distribution includes defining the energy function as $$P = \sum_{j=1}^{N} \sigma_i^2$$

for a set of conductivity or admittivity values $\sigma_j$ for j=1 to N, with N equal to the total number of values $\sigma_j$ used to define the conductivity or admittivity distribution;
   the forward model expressing the measured set of electrical signals as a function of the change in voltage values with respect to conductivity or admittivity is expressed as $$U_i = \sum_{j=1}^{N} J_{ij}\sigma_j$$

where $U_i$ is a vector comprising a total number of data elements, M, in the set of electrical signals measured at the electrodes, with i=1, 2, 3, ... M; and
   evaluating a function $F(\sigma_i)$ for which $$\frac{\partial F}{\partial \sigma_j} = 0 \quad \text{where} \quad F(\sigma) = \sum_{j=1}^{N}\sigma_j^2 - \sum_{i=1}^{M}\lambda_i[J_{i,j}\sigma_j - U_i]$$

such that the partial derivative of the difference between the energy function and a function based on the forward model equals zero, thereby determining a conductivity or admittivity distribution representative of a portion of the interior of the structure.

13. The method of claim 1 further including providing the image data to a display for viewing of an image representative of the interior of the structure.

14. A system for providing an image of an interior of a structure containing multiple regions having different conductivities or admittivities which influence transmission of electrical signals through the structure, comprising:
   a series of electrodes positioned along an external surface of the structure and along a plane passing through the structure;
   signal circuitry configured to provide a series of electrical signal sets for input to the electrodes, each signal set comprising an electrical signal pattern for input to each of the electrodes so that with sequential application of each of the electrical signal sets to the electrodes, application of each signal set generates a rotating electric field within the structure and for obtaining, in response to application of each signal set, a measured set of electrical signals from the electrodes;
   circuitry including a processor configured to calculate, with the measured set of electrical signals, a conductivity or admittivity distribution representative of the interior of the structure in a region of the structure about which the electrodes are positioned and for determining image data representative of the interior of the structure including two or more regions having different conductivities or admittivities, wherein calculation of the conductivity or admittivity distribution includes defining an energy function based on the conductivity distribution and a forward model expressing the measured set of electrical signals as a function of the change in voltage values with respect to conductivity and requiring that the partial derivative of the difference between the energy function and a function based on the forward model equal zero.

\* \* \* \* \*

UNITED STATES PATENT AND TRADEMARK OFFICE
CERTIFICATE OF CORRECTION

PATENT NO.        : 8,054,094 B1                                  Page 1 of 1
APPLICATION NO.   : 12/797653
DATED             : November 8, 2011
INVENTOR(S)       : Langoju et al.

It is certified that error appears in the above-identified patent and that said Letters Patent is hereby corrected as shown below:

In Column 3, Line 53, delete "12," and insert -- $12_i$ --, therefor.

In Column 3, Line 55, delete "12," and insert -- $12_i$ --, therefor.

In Column 6, Line 66, delete "V," and insert -- $V_i$ --, therefor.

Signed and Sealed this
Sixth Day of March, 2012

David J. Kappos
*Director of the United States Patent and Trademark Office*